United States Patent
Imura et al.

(10) Patent No.: US 9,035,112 B2
(45) Date of Patent: May 19, 2015

(54) PROCESS FOR PRODUCING 2-CHLORO-1,3,3,3-TETRAFLUOROPROPENE

(71) Applicant: Central Glass Company, Limited, Ube-shi, Yamaguchi (JP)

(72) Inventors: Hideaki Imura, Saitama (JP); Yoshio Nishiguchi, Saitama (JP); Masamune Okamoto, Fujimino (JP); Tatsuya Hayasaka, Saitama (JP); Minako Oomura, Fujimino (JP); Satoru Okamoto, Kawagoe (JP); Naoto Takada, Saitama (JP)

(73) Assignee: Central Glass Company, Ltd., Ube-shi (JP)

( * ) Notice: Subject to any disclaimer, the term of this patent is extended or adjusted under 35 U.S.C. 154(b) by 0 days.

(21) Appl. No.: 14/273,113

(22) Filed: May 8, 2014

(65) Prior Publication Data

US 2015/0038749 A1 Feb. 5, 2015

(30) Foreign Application Priority Data

May 9, 2013 (JP) .................. 2013-099596
Apr. 17, 2014 (JP) .................. 2014-085456

(51) Int. Cl.
*C07C 17/23* (2006.01)
*C07C 17/383* (2006.01)
*C07C 21/18* (2006.01)
*C07C 17/25* (2006.01)

(52) U.S. Cl.
CPC .............. *C07C 17/383* (2013.01); *C07C 17/23* (2013.01)

(58) Field of Classification Search
CPC ...... C07C 17/23; C07C 17/25; C07C 17/383; C07C 21/18

USPC .................................................. 570/135, 155
See application file for complete search history.

(56) References Cited

U.S. PATENT DOCUMENTS

| | | | |
|---|---|---|---|
| 3,499,089 A | 3/1970 | Regan | |
| 2012/0172636 A1 | 7/2012 | Pokrovski et al. | |
| 2012/0310019 A1* | 12/2012 | Wang et al. | 570/155 |
| 2013/0023703 A1* | 1/2013 | Eicher et al. | 570/135 |
| 2013/0150632 A1* | 6/2013 | Zhai et al. | 570/151 |

FOREIGN PATENT DOCUMENTS

JP 2013-103890 A 5/2013

OTHER PUBLICATIONS

Haszeldine, Robert N. et al. "Polyfluoroalkyl Derivatives of Silicon. Part XIV. Reaction of Tri-chlorosilane with 1,3,3,3-Tetrafluoropropene and 2-Chloro-1,3,3,3-tetra-fluoropropene." J.C. S. Dalton, Feb. 17, 1975, 3 pages.

\* cited by examiner

*Primary Examiner* — Shailendra Kumar

(74) *Attorney, Agent, or Firm* — Crowell & Moring LLP

(57) ABSTRACT

Disclosed is a process for producing 2-chloro-1,3,3,3-tetrafluoropropene (1224), including a first step of separating 2,3-dichloro-1,1,1,3-tetrafluoropropane (234da) into erythro form and threo form, and a second step of bringing the separated erythro form or threo form in contact with a base to obtain 2-chloro-1,3,3,3-tetrafluoropropene (1224). The first step is a step of separating 234da by distillation to achieve a separation into a fraction containing mainly erythro form and a fraction containing mainly threo form. In the second step, 1224 cis form is obtained from the erythro form, and 1224 trans form is obtained from the threo form. By this process, it is possible to selectively and efficiently produce cis form or trans form of 2-chloro-1,3,3,3-tetrafluoropropene (1224).

12 Claims, No Drawings

PROCESS FOR PRODUCING 2-CHLORO-1,3,3,3-TETRAFLUOROPROPENE

TECHNICAL FIELD

The present invention relates to a process for producing 2-chloro-1,3,3,3-tetrafluoropropene. Specifically, the present invention relates to a process for producing 2-chloro-1,3,3,3-tetrafluoropropene to efficiently produce either a trans form or a cis form. 2-chloro-1,3,3,3-tetrafluoropropene is useful as a detergent, a refrigerant, or a heat medium or high-temperature working fluid for heat pumps, etc.

In place of specified chlorofluorocarbons judged in Montreal Protocol as having a strong effect particularly on the ozone layer destruction, there have been synthesized and used various alternative chlorofluorocarbons having a less fear of the ozone layer destruction. In recent years, there has been a demand for alternative chlorofluorocarbons to have a shorter life in the air to have a shorter effect on the global warming.

2-chloro-1,3,3,3-tetrafluoropropene containing a double bond in the molecule rapidly decomposes in the air through a reaction between the double bond and OH radical or the like in the air. Therefore, it has a low global warming potential and a less fear of the ozone layer destruction. 2-chloro-1,3,3,3-tetrafluoropropene has geometrical isomers of trans form and cis form. In the following, in the case of a mixture of trans form and cis form of 2-chloro-1,3,3,3-tetrafluoropropene or in the case of not considering cis form and trans form, it may be referred to as 1224. Trans form may be referred to as 1224E, and cis form may be referred to as 1224Z.

As isomers of 1224, trans form (1224E) has a boiling point of 23° C., and cis form (1224Z) has a boiling point of 17° C. Chlorofluorocarbons having boiling points in the vicinity of room temperature (about 20° C.) are preferable to be used as foaming agent, solvent, refrigerant or working fluid, etc.

For example, trans form (1224E) having a boiling point of 23° C. is, as compared with cis form (1224Z) having a boiling point of 17° C., superior as a foaming agent of heat insulating materials made of rigid urethane foams. Furthermore, it hardly generates a bumping even in a high-temperature summer, etc. Therefore, it is superior as a foaming agent of foaming-in-place type heat insulating materials, which are produced at house construction sites. In contrast with trans form (1224E), cis form (1224Z) having a boiling point of 17° C. is used as a foaming agent of heat insulating materials for refrigerator, etc.

Furthermore, since 1224 has a boiling point in the vicinity of room temperature, it is preferably used as a heat medium or high-temperature working fluid for heat pumps. In the case of using as a high-temperature working fluid for heat pumps, even a small difference in boiling point makes a difference in terms of coefficient of performance (COP), which is the value representing a cooling/heating capacity per 1 kw of power consumption, or heat transportation capacity in refrigerating cycle, etc. In the use as a high-temperature working fluid, a suitable boiling point becomes different depending on the heat cycle condition. Therefore, it is preferable to select trans form (1224E) or cis form (1224Z) depending on the use.

As to trans form (1224E) and cis form (1224Z) having different boiling points, it is preferable to obtain only one of them in the production. However, a technique to selectively and separately make trans form (1224E) and cis form (1224Z) has not been established, and there is no knowledge thereon.

As techniques for obtaining 1224, it is possible to cite the following Patent Publications 1-3 and Non-patent Publication 1. Each of them is not a technique to selectively and separately make trans form (1224E) and cis form (1224Z).

It is described in Non-patent Publication 1 that, as a specific synthesis example of 1224, a photochemical chlorination of 1,3,3,3-tetrafluoropropene (in the following, it may be referred to as 1234) is conducted to synthesize 2,3-dichloro-1,1,1,3-tetrafluoropropane (in the following, it may be referred to as 234da), and 234da is subjected to a dehydrochlorination by potassium hydroxide to synthesize 1224. According to the description on page 2294, yield of the step for producing 234da by the photochemical chlorination step of 1234 is as good as 98%, but yield of 1224 by the dehydrochlorination step of 234da is 69%.

Patent Publication 1 describes a process for synthesizing 2-chloro-1,1,1,3,3-pentafluoropropane (in the following, it may be referred to as 235da), which is a raw material of 1224.

It is described in Patent Publication 2 that 1224 is formed by bringing a trans-1-chloro-3,3,3-trifluoropropane (in the following, it may be referred to as 1233E) containing 235da as a trace impurity into contact with a base.

It is described in Patent Publication 3 that, when producing 1-chloro-3,3,3-trifluoropropene, formation of chlorotetrafluoropropene ($C_3HClF_4$) as a by-product is reduced by conducting a fluorination reaction using, as a raw material, $CCl_3$—$CH_2$—$CHCl_2$ (240fa) in which $CCl_3$—$CHCl$—$CHCl_2$ (in the following, it may be referred to as 240da) as an impurity has been adjusted to 0.08% or lower. $C_3HClF_4$ has 13 isomers, but there is no description of which isomer was.

In a conventional process for producing 2-chloro-1,3,3,3-tetrafluoropropene (1224), 1224 is obtained as a mixture of cis form (1224Z) and trans form (1224E). Therefore, it has been necessary to separate that into cis form (1224Z) and trans form (1224E) by a method such as distillation. However, even if one tries to selectively take out either trans form (1224E, boiling point: 23° C.) or cis form (1224Z, boiling point 17° C.) by distillation, difference of boiling point in the vicinity of ordinary temperature (about 20° C.) is only 6° C. Therefore, it has not been easy to separately take them out. Thus, it has not been possible to efficiently obtain cis form (1224Z) or trans form (1224E).

PRIOR ART PUBLICATIONS

Patent Publications

Patent Publication 1: U.S. Pat. No. 3,499,089
Patent Publication 2: Japanese Patent Application Publication 2013-103890
Patent Publication 3: US Patent Application Publication 2012-0172636

Non-Patent Publications

Non-patent Publication 1: Journal of the Chemical Society, Dalton Transactions: Inorganic Chemistry, Vol. 1975, No. 21, PP. 2292-2294 (1975)]

SUMMARY OF THE INVENTION

It is an object of the present invention to provide, in the production of 2-chloro-1,3,3,3-tetrafluoropropene, a process for producing 2-chloro-1,3,3,3-tetrafluoropropene to produce either trans form (1224E) or cis form (1224Z).

Furthermore, it is an object of the present invention to provide trans form (1224E) or cis form (1224Z) without formation of by-products in the production of 2-chloro-1,3,3,3-tetrafluoropropene.

In 2,3-dichloro-1,1,1,3-tetrafluoropropane (234da), there exist threo form and erythro form as diastereoisomers as geometrical isomers. As a result of an eager study, the present inventors have found that it is possible to selectively produce trans form (1224E) from 234da threo form and cis form (1224Z) from 234da erythro form by separating into threo form and erythro form by distillation and then conducting a dehydrochlorination reaction by a contact with a base, thereby completing the present invention.

The present invention includes the following Inventions 1 to 12.

Invention 1

A process for producing 2-chloro-1,3,3,3-tetrafluoropropene (1224), comprising:

a first step (separation step) that is a separation step for separating 2,3-dichloro-1,1,1,3-tetrafluoropropane (234da) and is a step (1a) for taking out a component (A) having a molar ratio of threo form to erythro form of 100:0 to 80:20 or a step (1b) for taking out a component (B) having a molar ratio of threo form to erythro form of 0:100 to 20:80; and a second step of bringing the component (A) or the component (B) into contact with a base.

Invention 2

The production process of Invention 1, wherein the first step is a step (1a) of taking out a fraction (A) having a molar ratio of threo form to erythro form of 100:0 to 80:20 or a step (1b) of taking out a fraction (B) having a molar ratio of threo form to erythro form of 0:100 to 20:80.

Invention 3

The production process of Invention 1 or Invention 2, wherein the second step is a second step A of bringing component (A) having a molar ratio of threo form to erythro form of 100:0 to 80:20 into contact with the base, thereby obtaining 2-chloro-1,3,3,3-tetrafluoropropene (1224) having a molar ratio of trans form to cis form of 100:0 to 80:20.

Invention 4

The production process of Invention 1 or Invention 2, wherein the second step is a second step B of bringing component (B) having a molar ratio of threo form to erythro form of 0:100 to 20:80 into contact with the base, thereby obtaining 2-chloro-1,3,3,3-tetrafluoropropene (1224) having a molar ratio of trans form to cis form of 0:100 to 20:80.

Invention 5

The production process of Inventions 1-4, wherein the base has an acid dissociation constant (pKa) of 4.8 or greater.

Invention 6

The production process of Inventions 1-5, wherein the second step is a step conducted in the presence of a phase transfer catalyst.

Invention 7

The production process of any one of Inventions 1-5, wherein the base is an organic base.

Invention 8

The production process of Invention 7, wherein the base is an amine.

Invention 9

The production process of Inventions 1-8, wherein a reactive distillation is conducted in the second step.

Invention 10

A process for separating 2,3-dichloro-1,1,1,3-tetrafluoropropane (234da), in which a distillation of 2,3-dichloro-1,1,1,3-tetrafluoropropane (234da) is conducted, thereby achieving a separation into a fraction (A) having a molar ratio of threo form to erythro form of 100:0 to 80:20 and a fraction (B) having a molar ratio of threo form to erythro form of 0:100 to 20:80.

Invention 11

A process for producing a trans form (1224E) of 2-chloro-1,3,3,3-tetrafluoropropene, in which a threo form of 2,3-dichloro-1,1,1,3-tetrafluoropropane (234da) is brought into contact with a base.

Invention 12

A process for producing a cis form (1224Z) of 2-chloro-1,3,3,3-tetrafluoropropene, in which an erythro form of 2,3-dichloro-1,1,1,3-tetrafluoropropane (234da) is brought into contact with a base.

Advantageous Effect of the Invention

According a process for producing 2-chloro-1,3,3,3-tetrafluoropropene (1224) of the present invention, it is possible to selectively and efficiently produce trans form (1224E) and cis form (1224Z) of 1224.

DETAILED DESCRIPTION

In 2,3-dichloro-1,1,1,3-tetrafluoropropane (234da) as a raw material compound of 2-chloro-1,3,3,3-tetrafluoropropene (1224), there exist a threo form and an erythro form as diastereomers. Diastereomers refer to stereoisomers which are not enantiomers. In two adjacent asymmetric centers, a relative configuration analogous to the configuration of erythrose is referred to as erythro-form configuration, and one analogous to the configuration of threose is referred to as threo-form configuration. In Newman projection formula of an eclipsed form, a configuration with analogous groups eclipsing each other refers to an erythro form. In the following, a mixture of threo form and erythro form of 2,3-dichloro-1,1,1,3-tetrafluoropropane is simply referred to as 234da, the threo form is referred to as 234da threo form, and the erythro form is referred to as 234da erythro form.

As a result of an eager study, the present inventors have found that it is possible to concentrate 234da into a fraction (A) mainly containing 234da threo form and a fraction (B) mainly containing 234da erythro form by a distillation operation. In the present invention, "mainly containing" refers to that 234da threo form or 234da erythro form is 80% or more by mol % in the mixture of threo form and erythro form. Preferably, it is 90% or more. Specifically, in 234da, mainly containing threo form refers to that the molar ratio of threo form to erythro form is 100:0 to 80:20. Preferably, the ratio of threo form to erythro form is 100:0 to 90:10. Mainly containing erythro form refers to that the molar ratio of threo form to erythro form is 0:100 to 20:80. Preferably, the molar ratio of threo form to erythro form is 0:100 to 10:90.

According to the present inventors, boiling point measured by using a 234da threo form with a purity of 99.8% was 74° C., and boiling point measured by using a 234da erythro form with a purity of 99.4% was 70 C. As compared with a separation of trans form (1224E, boiling point: 23° C.) or cis form (1224Z, boiling point: 17° C.) of 1224, which has a boiling point close to room temperature, by distillation, it becomes possible to loosely set the pressurization condition, etc. Therefore, in the actual production of chemical plant or the like, it is easier to separately obtain trans form (1224E) and cis form (1224Z) of 1224 by a contact with a base, after conducting a separation into 234da erythro form and 234da threo form by a distillation operation.

According to the 1224 production process of the present invention, the present inventors have paid attention to that unexpectedly 234da as the raw material can be separated into 234da threo form and 234da erythro form as geometrical isomers by a distillation operation. Furthermore, we have found that trans form (1224E) of 1224 is obtained from 234da threo form, and cis form (1224Z) of 1224 is obtained from 234da erythro form, by producing 234da as the raw material, then conducting a distillation to achieve a separation into 234da threo form and 234da erythro form, and then making contacts with a base to conduct dehydrochlorination reactions. Furthermore, in the 1224 production process of the present invention, in the case of concentrating only threo form or concentrating only erythro form and then making a contact with a base to conduct a dehydrochlorination reaction, an isomerization cannot occur due to intramolecular steric hindrance between 234da threo form and 234da erythro form and also between trans form (1224E) of 1224 and cis form (1224Z) of 1224. By using the 1224 production process of the present invention, it becomes possible to selectively obtain either trans form (1224E) or cis form (1224Z), which is requested by the producer.

That is, the 1224 production process of the present invention provides a process for producing 2-chloro-1,3,3,3-tetrafluoropropene to obtain a 2-chloro-1,3,3,3-tetrafluoropropene (1224) mainly containing trans form by bring a fraction (A) with concentrated threo form, which has been obtained by a distillation of 2,3-dichloro-1,1,1,3-tetrafluoropropane (234da) formed of a mixture of erythro form and threo form, into contact with a base, and a process for producing 2-chloro-1,3,3,3-tetrafluoropropene to obtain a 2-chloro-1,3,3,3-tetrafluoropropene (1224) mainly containing cis form by bring a fraction (B) with concentrated erythro form into contact with a base.

Furthermore, in the 1224 production process of the present invention, with respect to the base used when obtaining 1224 from 234da by such dehydrochlorination reaction, there is specified an efficient base for accelerating the reaction and for obtaining a desired geometrical isomer with a high selectivity and a high yield, and there is selected a phase transfer catalyst for accelerating the reaction.

It is possible by the 2-chloro-1,3,3,3-tetrafluoropropene (1224) production process of the present invention to selectively produce trans form (1224E) and cis form (1224Z) of 1224.

Furthermore, it is possible in the 2-chloro-1,3,3,3-tetrafluoropropene (1224) production process of the present invention to obtain trans form (1224E) and cis form (1224Z) with high yields, without by-production of 1,2-dichloro-3,3, 3-trifluoropropene (CF$_3$CCl=CHCl, it may be referred to as 1223 in the following), by selecting a type of base to be brought into contact with 234da or by using a phase transfer catalyst as an additive.

In the following, Inventions 1-12 are explained in detail.

1. Reaction

Dehydrochlorination Reaction of 2,3-Dichloro-1,1,1,3-Tetrafluoropropane (234da)

234da is a hydrochlorofluorocarbon represented by CF$_3$CHClCHClF. As shown in the following reaction formulas, a dehydrochlorination reaction progresses by bringing 234da into contact with a base. With this, it is possible to synthesize 1224.

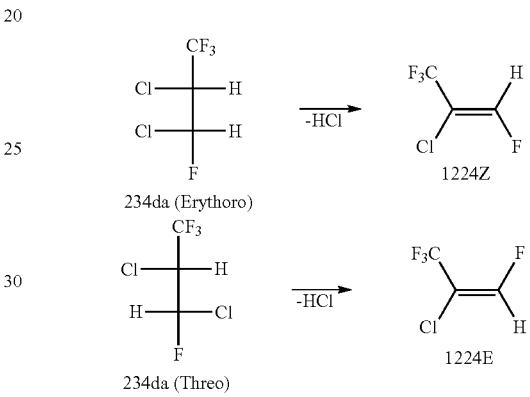

As shown in the above reaction formulas, when 234da threo form is brought into contact with a base, a dehydrochlorination reaction progresses, thereby selectively forming the trans form (1224E). When 234da erythro form is brought into contact with a base, a dehydrochlorination reaction progresses, thereby selectively forming the cis form (1224Z). In the 1224 production process of the present reaction, after a previous separation into erythro form and threo form of 234da, they are brought into contact with a base. With this, it is possible to selectively produce the cis form (1224Z) from 234da erythro form and the trans form (1224E) from 234da threo form.

In case that a producer wants to have 1224 and 1,2-dichloro-3,3,3-trifluoropropene (1223) at the same time, it is possible to use the photochemical chlorination process described in Non-patent Publication 1. However, in the case of a desire only for 1224, when using the photochemical chlorination process described in Non-patent Publication 1, there occurs a production of 1223 as a by-product by a dehydrofluorination reaction, thereby lowering yield of 1224. Furthermore, in a conventional technology in which 234da without a separation into erythro form and threo form was brought into contact with a base, there occurred a production of 1223 as a by-product by the dehydrofluorination (for example, Reference Example of the present specification).

As shown in the following chemical formula, even in the 1224 production process of the present invention, there is a fear of by-production of 1223.

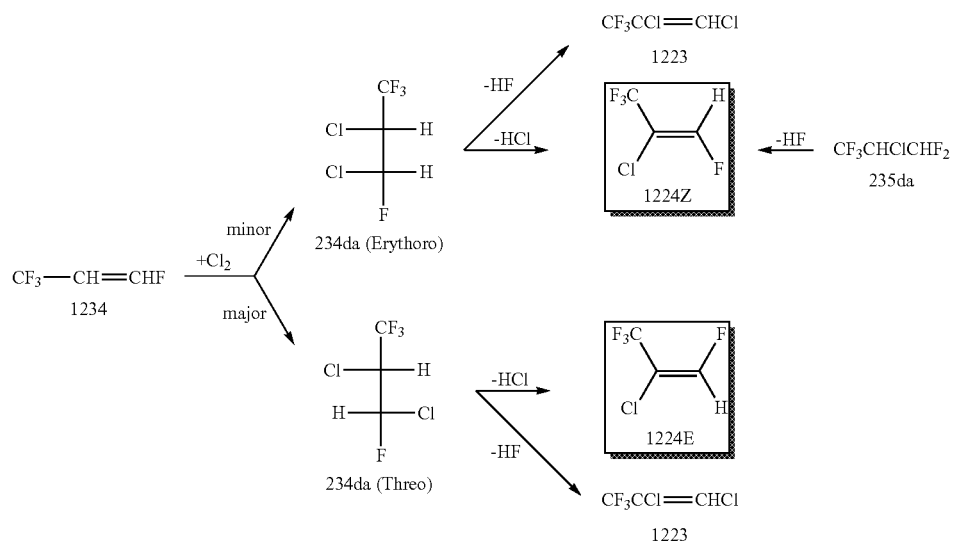

In the process for producing 1224 of the present invention, the selection of usage of the base and the reaction conditions is important in order to prevent by-production of 1223. Relative to one equivalent of 234da as the raw material, it is recommended that usage of the base is preferably from one equivalent to two equivalents, more preferably from one equivalent to 1.5 equivalents. In the case of excessively using the base, side reactions may occur. In the case of being less than one equivalent, the reaction may not be completed.

For example, in the case of using an inorganic base, etc., yield of 1224 may be lowered by by-production of 1223 caused by the progress of a dehydrofluorination reaction of 234da. In such case, it is preferable to add a third component to accelerate contact between 234da and the base. For example, there is shown as an example a phase transfer catalyst or a water-soluble organic compound that dissolves both 234da and water.

As compared with the water-soluble organic matter, a phase transfer catalyst achieves an advantageous effect by adding a small amount. Therefore, it is preferable to use a phase transfer catalyst.

The phase transfer catalyst can be exemplified by quaternary ammonium compounds, such as ammonium fluoride, ammonium chloride, ammonium bromide, ammonium iodide or ammonium hydroxide, crown ethers, calixarenes, cyclophanes, cyclodextrins, phosphonium compounds, or pyridinium compounds. Specifically, it can be exemplified by tetrabutylammonium fluoride, benzyldimethylalkylammonium chloride, 1-butyl-1-methylpyrrolidinium chloride, phenyltriethylammonium chloride, 1-butyl-1-methylpiperidinium bromide, trimethyl-3-trifluoromethylphenylammonium bromide, trimethyl-α,α,α-trifluoro-m-tolylammonium hydroxide, hexadecyltrimethylammonium hydroxide, trimethylphenylammonium iodide, 2,3-benzo-1,4,7,10-tetraoxadodec-2-ene, 24-crown 8-ether, triphenyl(2-chlorobenzyl)phosphonium chloride, or 4-(dimethylamino)-1-(triphenylmethyl) pyridinium chloride. In particular, tetrabutylammonium bromide is preferable, since it achieves an advantageous effect by a small amount.

The addition of the phase transfer catalyst is preferably from 0.01 mol % to 10 mol % relative to 234da. If the addition is less than 0.01%, a sufficient addition effect may not be found. Even if the addition is greater than 10 mol %, a further effect can be not expected. With this, not only the phase transfer catalyst is wasted, but also there increases a cumbersome work such as cleaning of the reactor after the reaction. Therefore, the addition by greater than 10 mol % is not necessary.

The water-soluble organic matter refers to an organic matter that is not separated when mixing it with water by a volume ratio of 1:1. Specifically, ketones such as acetone, ethers, or amides are preferable. It is preferable that the addition of the water-soluble organic matter is from 5 mol % to 200 mol %, relative to 100 mol % of 234da. If it is less than 5 mol %, a sufficient effect for improving selectivity of 234da may not be obtained. If it is greater than 200 mol %, productivity per unit volume of the reactor lowers.

The reaction temperature is from −5° C. to 100° C., preferably from 0° C. to 50° C. If it is lower than −5° C., the reaction rate is slow, thereby taking time to obtain a sufficient amount of 1224. Alternatively, the aqueous solution may be frozen. Although it is also possible to add an organic solvent or the like to prevent freezing of the aqueous solution, a separation from 2-chloro-1,3,3,3-tetrafluoropropene (1224) may become difficult, or waste may increase. If it exceeds 100° C., there is a fear that side reactions occur to produce by-products. Therefore, it is not preferable.

The reaction progresses even under compression, decompression or ordinary pressure. Ordinary pressure is convenient in an industrial scale, that is, an industrial production in an industrial plant. Boiling point of cis form (1224Z) of 2-chloro-1,3,3,3-tetrafluoropropene is 17° C., and boiling point of trans form (1224E) is 23° C. In the case of conducting the operation at a reaction temperature higher than these, it is preferable to conduct the separation by the reaction under compression or by using a reactive distillation to conduct the reaction while taking out the product by distillation. The reactive distillation is convenient in operation, and yield of the target product is high. It is preferable to gradually add a basic aqueous solution heated at a temperature of from 20° C. to 50° C. to 2,3-dichloro-1,1,1,3-tetrafluoropropane (234da) and gradually take out 2-chloro-1,3,3,3-tetrafluoropropene (1224), which is generated as a low-boiling-point gas, with stirring. Taking out by a simple distillation is also possible, but mass production is more possible by a taking out using a distillation column. This is advantageous in industrial production. Such reactive distillation method is a superior method.

Furthermore, it becomes possible to complete the reaction by adding a base, by selecting the reaction condition, as in Examples of the present specification. After completing the reaction, it is preferable to take out the raw material and the product in a dissolved fraction by a flash distillation by heating for about 60 minutes.

According to need, it is possible to separate the product into cis form (1224Z) or trans form (1224E) of 2-chloro-1,3,3,3-tetrafluoropropene through ordinary steps, such as washing with water, drying, distillation and adsorption purification.

In the present invention, it is preferable that a fraction(s) except the target compound separated by a distillation purification is recycled as the raw material, is used as an intermediate of medicines and agricultural chemicals or as a polymer raw material, or is used by conducting isomerization, disproportionation reaction, etc.

2. Raw Material

Production of
2,3-Dichloro-1,1,1,3-Tetrafluoropropane (234da)

The method for producing 234da is not particularly limited. For example, as described in Non-patent Publication 1, it is possible to easily obtain 234da with a high yield by photochemical reaction. Furthermore, it is possible to easily produce 234da by photochemical reaction of 1,3,3,3-tetrafluoropropene (in the following, may be referred to as 1234), which is commercially produced. 1234 as the raw material may be cis form, trans form or a mixture of cis form and trans form. It is convenient to conduct a photochemical reaction by irradiating 1234 with ultraviolet rays of a high-pressure mercury lamp to produce 234da. It is optional to use a method other than photochemical reaction, for example, a method using radical initiator or catalyst.

As shown in the section of "Preparation of 2,3-dichloro-1,1,1,3-tetrafluoropropane (234da)" of Preparation Example 1 of the present specification, a threo form and an erythro form are formed as diastereomers of 234da by conducting a photochemical chlorination of trans-1,3,3,3-tetrafluoro-1-propene at −78° C. Under the present reaction condition, the ratio of the threo form to the erythro form becomes roughly 2:1.

Furthermore, according to Non-patent publication 1, it is possible to synthesize 234da by conducting a photochemical chlorination of 1,3,3,3-tetrafluoro-1-propene, which is on the market as a covering gas of a magnesium melting furnace, etc.

3. Separation by Distillation of a Mixture of 234da Threo Form and 234da Erythro Form as the Raw Material Compounds It is possible to separate a mixture of 234da threo form and 234da erythro form by distillation into a high-boiling-point fraction (A) containing mainly 234da threo form having a boiling point of 74° C. and a low-boiling-point fraction (B) containing mainly 234da erythro form having a boiling point of 70° C. After separation into a high-boiling-point fraction (A) containing mainly 234da threo form and a low-boiling-point fraction (B) containing mainly 234da erythro form, it becomes possible to obtain a product containing mainly cis form (1224Z) and a product containing mainly trans form (1224E) as the target compound by contact with a base.

By contact with a base to conduct a dehydrochlorination reaction without separation into 234da threo form and 234da erythro form, both trans form (1224E) and cis form (1224Z) are formed, resulting in forming a mixture of these. Even if it is tried to separate a mixture of 1224 into trans form (1224E, boiling point: 23° C.) and cis form (1224Z, boiling point: 17° C.) by a distillation operation, it is difficult to conduct distillation by using an atmospheric pressure distillation column and a vacuum distillation column, since the boiling points are around room temperature (about 20° C.). Therefore, it is necessary to conduct a pressure distillation. Thus, it is necessary to use a pressure-proof distillation column. Furthermore, it is necessary to use a special distillation column with many stages and a receiver of each stage that can be cooled, in order to achieve a complete separation. In particular, in the summer, it is necessary to adjust the distillation conditions for maintaining precision of pressure distillation.

On the other hand, 234da threo form (boiling point: 74° C.) and 234da erythro form (boiling point: 70° C.) are high in boiling point. It is possible to separate a mixture of these into 234da threo form (boiling point: 74° C.) and 234da erythro form (boiling point: 70° C.) by using an atmospheric pressure or vacuum distillation column. It is also possible to select pressure distillation. In the distillation, it is possible to achieve a separation into 234da threo form (boiling point: 74° C.) and 234da erythro form (boiling point: 70° C.) with high purity as the number of stages increases. It is preferable to use a distillation column with 10 to 100 stages.

Regarding base used in 1224 production process of the present invention

The inorganic base used in the 2-chloro-1,3,3,3-tetrafluoropropene (1224) production process of the present invention can be exemplified by hydroxides, carbonates, hydrogencarbonates, phosphates, and acetates of alkali metals, such as lithium, sodium or potassium, and hydroxides of alkali-earth metals, such as calcium. The organic base can be exemplified by alkali metal salts of $C_{1-6}$ carboxylic acids, or $C_{3-18}$ tertiary amines.

For example, the inorganic base can be exemplified by sodium hydroxide, potassium hydroxide, calcium hydroxide, lithium carbonate, lithium hydrogencarbonate, lithium phosphate, sodium carbonate, sodium hydrogencarbonate, sodium phosphate, potassium carbonate, potassium hydrogencarbonate, potassium phosphate, lithium acetate, sodium formate, sodium acetate, potassium formate, or potassium acetate.

For example, the organic base can be exemplified by tertiary amines selected from trimethylamine, triethylamine, tri-n-propylamine, tri-isopropylamine, tri-n-butylamine, tri-isobutylamine, tri-sec-butylamine, tri-tert-butylamine, tri-n-amylamine, tri-isoamylamine, tri-sec-amylamine, tri-tert-amylamine, N,N,N',N'-tetramethylethylenediamine, N,N,N',N'-tetramethylpropane-1,3-diamine, tetramethylguanidine, N-methyldiethylamine, N-methyldi-n-propylamine, N-methyldiisopropylamine, N-methyldi-n-butylamine, N-methyldiisobutylamine, N-methyldi-tert-butylamine, N,N-diisopropylbutylamine, N,N-dimethyl-n-octylamine, N,N-nonylamine, N,N-dimethyldecylamine, N,N-dimethylundecylamine, N,N-dimethyldodecylamine, or N-methyldihexylamine. A cyclic amine can be exemplified by tetramethylguanidine, N,N'-dimethylpiperazine, 1,8-diazabicyclo[5.4.0]-7-undecene (DBU), 1,4-diazabicyclo[2.2.2]octane (DABCO), or bis(2-dimethylaminoethyl)ether, etc.

In the 1224 production process of the present invention, the selection of the base to be used is important.

In both of the inorganic base and the organic base, the reaction rate may become extremely low by using a base (conjugate acid) having an acid dissociation constant pKa of less than 4 (pKa<4). With this, the reaction may substantially not progress. For example, the reaction does almost not progress by using potassium dihydrogenphosphate ($KH_2PO_4$), in which acid dissociation constant is 2 (pKa=2). In contrast, the reaction progresses by using potassium acetate (AcOK), in which pKa=4.8, and dipotassium hydrogenphosphate ($K_2HPO_4$), in which pKa=7.2. In particular, it is possible to obtain high reaction rates by using potassium carbonate ($K_2CO_3$) and potassium phosphate ($K_3PO_4$), in which pKa is not lower than 10. Thus, it is possible to complete the reaction to increase yield of 1224. In particular, the reaction rate is high when using sodium hydroxide (NaOH), potassium hydroxide (KOH) and calcium hydroxide (Ca(OH)$_2$), in which pKa is not less than 15. Thus, it is possible to use a base having a pKa of not less than 4.8, more preferably that having a pKa of not less than 7, still more preferably that having a pKa of not less than 10, the most preferably that having a PKa of not less than 15. The values of pKa of these compounds are described in Revised 5th-edition Kagaku Binran, edited by The Chemical Society of Japan, etc.

Acid dissociation constant (pKa) is a constant in which proton donating capacity of Broensted acid is comparatively expressed provided that water molecule is a standard proton acceptor (base). In the present invention, acid dissociation constant (pKa) is expressed provided that the base used in the 1224 production process of the present process is a conjugate acid.

In the case of using an inorganic base, it is preferable to use a phase transfer catalyst in order to suppress by-production of 1,2-dichloro-3,3,3-trifluoropropene $CF_3CCl=CHCl$ (1223) and increase yield of 2-chloro-1,3,3,3-tetrafluoropropene (1224) as the target substance.

In contrast with using an inorganic base, in the case of using an organic base, by-production of 3-trifluoropropene $CF_3CCl=CHCl$ is small even if not using a phase transfer catalyst. Therefore, it is preferable. In particular, when using 1,8-diazabicyclo-[5,4,0]-7-undecene (DBU), in which acid dissociation constant (pKa) is 12, as an organic base, it is possible to obtain 2-chloro-1,3,3,3-tetrafluoropropene (1224) with high yield. Furthermore, in the case of using tri-n-butylamine (n-Bu$_3$N), n-Bu$_3$NCl is formed. Since this n-Bu$_3$NCl has an action analogous to that of the phase transfer catalyst, it has an effect for improving reactivity or selectivity.

EXAMPLES

In the following, the present invention is concretely demonstrated by Examples, but embodiments of the present invention are not limited to this. Unless otherwise noted, composition of organic matter was measured by an FID detector using gas chromatography, and the recorded areal % was expressed as %. Furthermore, the third decimal place was round off. For example, in the case of being 0.004 areal %, it was expressed as 0.00%.

Preparation Example 1

Preparation of 2,3-Dichloro-1,1,1,3-Tetrafluoropropane (234da)

A bottom portion of a glass reactor equipped with a gas inlet and having a capacity of 2000 ml was immersed and cooled in an acetone bath having a temperature of −78° C. and containing dry ice, followed by charging the reactor with 901.86 g (7.90 mol) of trans-1,3,3,3-tetrafluoropropene as the raw material. Under an immersion in the acetone bath of −78° C., the reaction was started by bubbling chlorine (Cl$_2$) into the reactor at a supply rate of 1.70 g/min. Then, while a photoirradiation was conducted by a high-pressure mercury lamp from the outside of the reactor, the raw material and chlorine in the reactor were stirred by a magnetic stirrer. Five hours and thirty minutes later, the reaction was terminated. The total amount of chlorine introduced was 560.5 g (7.90 mol). The reaction system was washed with water, saturated sodium hydrogencarbonate aqueous solution, and saturated brine, thereby obtaining a reaction product (1427.0 g) containing 234da as the target product. As composition of the reaction product was measured by a gas chromatograph, 234da was found to be 98.7% (the total of threo form and erythro form) in the composition. Yield of 234da was 96.3%. Then, the above reaction operation was repeated five times to obtain a necessary amount of the reaction product. As a result of measuring each of the products obtained by the five reaction operations by gas chromatography, the molar ratio of threo form to erythro form was roughly 2:1. By these five reaction operations, there was obtained 234da containing 65.1% of threo form, 33.7% of erythro form, and 1.2% of other impurities.

In the following, Fischer projections, Newman projections, and the results of coupling analysis of NMR spectrum of threo form and erythro form are shown. The analysis result of NMR spectrum of threo form is shown in Table 1. The analysis result of NMR spectrum of threo form is shown in Table 2.

<Threo Form>

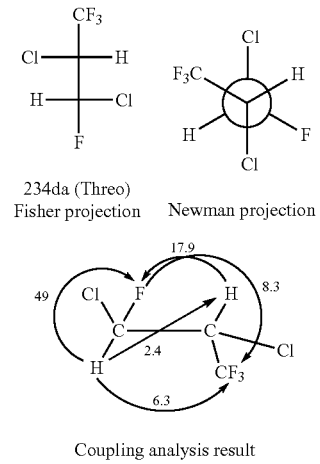

234da (Threo)
Fisher projection    Newman projection

Coupling analysis result

TABLE 1

| Observed nucleus | Chemical shift (ppm) | Coupling constant (Hz) | Assignment |
|---|---|---|---|
| $^{19}F$ | −35.7 | dd (6.2, 8.3) | C$\underline{F}_3$—CHCl—CFHCl |
|  | −110.7 | ddq (17.9, 49.0, 8.3) | CF$_3$—CHCl—C$\underline{F}$HCl |
| $^{13}C$ | 59.9 | dq (25.7, 32.8) | CF$_3$—$\underline{C}$HCl—CFHCl |
|  | 97.4 | dq (247.6, 2.0) | CF$_3$—CHCl—$\underline{C}$FHCl |
|  | 121.9 | dq (4.8, 280.2) | $\underline{C}$F$_3$—CHCl—CFHCl |
| $^1H$ | 4.4 | ddq (2.4, 17.9, 6.3) | CF$_3$—C$\underline{H}$Cl—CFHCl |
|  | 6.5 | dd (2.4, 49.0) | CF$_3$—CHCl—CF$\underline{H}$Cl |

<Erythro Form>

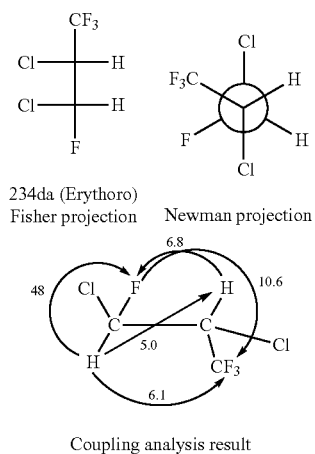

234da (Erythoro)
Fisher projection    Newman projection

Coupling analysis result

TABLE 2

| Observed nucleus | | Chemical shift (ppm) | Coupling constant (Hz) | Assignment |
|---|---|---|---|---|
| $^{19}F$ | Minor | −35.1 | dd (6.1, 10.7) | C$\underline{F}_3$—CHCl—CFHCl |
| | nor | −103.8 | ddq (6.8, 48.2, 10.6) | CF$_3$—CHCl—C$\underline{F}$HCl |
| $^{13}C$ | Minor | 61 | dq (21.5, 33.1) | CF$_3$—$\underline{C}$HCl—CFHCl |
| | nor | 95.3 | dq (250.6, 2.5) | CF$_3$—CHCl—$\underline{C}$FHCl |
| | | 122.1 | dq (0.5, 280.5) | $\underline{C}$F$_3$—CHCl—CFHCl |
| $^{1}H$ | Minor | 4.5 | ddq (5.1, 6.8, 6.1) | CF$_3$—C$\underline{H}$Cl—CFHCl |
| | nor | 6.4 | dd (4.9, 48.3) | CF$_3$—CHCl—CF$\underline{H}$Cl |

Preparation Example 2

Distillation Separation of 234Diastereomers (Threo Form and Erythro Form)

By distilling 3560.6 g of 234da (65.1% of threo form and 33.7% of erythro form) obtained by the above preparation operation with a distillation column filled with a Helipack No. 2 as a filler and having theoretical 50 stages, it was separated into a fraction (A) containing mainly threo form and a fraction (B) containing mainly erythro form. Specifically, there were obtained 882 g of the fraction (A) (5.8% of erythro form and 94.2% of threo form) as a high-boiling-point fraction, in which threo form had been concentrated, and which contained mainly threo form, and 482 g of the fraction (B) (89.9% of erythro form and 10.1% of threo form) as a low-boiling-point fraction, in which erythro form had been concentrated, and which contained mainly erythro form.

There were obtained a high-purity threo form (98.97% of threo form and 1.02 g of erythro form) by distilling again a portion of the fraction A, and a high-purity erythro form (99.68% of erythro form and 0.24% of threo form) by distilling a portion of the fraction B.

Example 1

Dehydrochlorination Reaction of Fraction a Containing Mainly 234da Threo Form

Using sodium hydroxide having an acid dissociation constant (pKa) of not less than 15 as an inorganic base and using tetrabutylammonium bromide (TBAB) as a phase transfer catalyst, there was conducted a dehydrochlorination reaction of fraction A containing mainly 234da threo form, thereby obtaining 1224 containing mainly trans form (1224E).

A 1 liter capacity, four-necked flask equipped with a Dimroth, a 500 ml capacity dropping funnel, a thermometer, and a stirrer was charged with 2.00 g (0.006 mol) of tetrabutylammonium bromide as a phase transfer catalyst and 555.07 g (3.0 mol) of the fraction (A) (94.2% of threo form and 5.8% of erythro form) which contained mainly threo form and had been obtained in Preparation Example 2. While refluxing the content by allowing a coolant of −15° C. to flow through the Dimroth, a bottom portion of the flask was immersed in a water bath having a water temperature of 0-5° C., and stirring of the content in the flask was started. From the dropping funnel, 505.02 g (3.16 mol) of sodium hydroxide aqueous solution having a concentration of 25 mass % was gradually added dropwise to the flask by spending 123 minutes. After stirring the content in the flask at the same temperature for 1 hour, it was cooled with iced water. A distillation recovery was conducted by removing the Dimroth and the dropping funnel and changing to a simple distillation apparatus equipped with a Vigreux column having a length of 30 cm, thereby obtaining 429.95 g of a product containing 2-chloro-1,3,3,3-tetrafluoropropene (1224). Composition of the product was measured by gas chromatography. With this, it was found to be 4.5% of cis form (1224Z), 95.5% of trans form (1224E), and 0.02% of 234da.

Isolation of Trans Form (1224E)

The obtained product was subjected to an adsorptive drying treatment by Molecular Sieve 4A (Molecular Sieve is a trademark) as a synthetic zeolite, thereby obtaining 399.89 g of 2-chloro-1,3,3,3-tetrafluoropropene (1224). As it was purified by distillation with a distillation column filled with Helipack No. 1 and having theoretical 80 stages, there was obtained 303.96 g of a fraction containing 0.1% of cis form (1224Z) and 99.9% of trans form (1224E).

Example 2

Dehydrochlorination Reaction of Fraction B Containing Mainly 234da Erythro Form

Using sodium hydroxide having an acid dissociation constant (pKa) of not less than 15 as an inorganic base and using tetrabutylammonium bromide as a phase transfer catalyst, there was conducted a dehydrochlorination reaction of fraction B containing mainly erythro form of 234da (2,3-dichloro-1,1,1,3-tetrafluoropropane), thereby obtaining 1224 (2-chloro-1,3,3,3-tetrafluoropropene) containing mainly cis form (1224Z).

A 500 ml capacity, four-necked flask equipped with a Dimroth, a 300 ml capacity dropping funnel, a thermometer, and a stirrer was charged with 1.26 g (0.004 mol) of tetrabutylammonium bromide as a phase transfer catalyst and 350.13 g (1.98 mol) of the fraction (B) (89.9% of erythro form and 10.1% of threo form) which contained mainly erythro form and had been obtained in Preparation Example 2. While refluxing the content by allowing a coolant of −15° C. to flow through the Dimroth, a bottom portion of the flask was immersed in a water bath having a water temperature of 0-5° C., and stirring of the content in the flask was started. From the dropping funnel, 332.64 g (2.08 mol) of sodium hydroxide aqueous solution having a concentration of 25 mass % was gradually added dropwise to the flask by spending 88 minutes. After stirring the content in the flask at the same temperature for 1 hour, it was cooled with iced water. A distillation recovery was conducted by removing the Dimroth and the dropping funnel and changing to a simple distillation apparatus equipped with a Vigreux column having a length of 30 cm, thereby obtaining 273.96 g of a product containing 2-chloro-1,3,3,3-tetrafluoropropene (1224). Composition of the product was measured by gas chromatography. With this, it was found to be 89.0% of cis form (1224Z) and 11.1% of trans form (1224E).

Isolation of Cis Form (1224Z)

The obtained product was subjected to an adsorptive drying treatment by Molecular Sieve 4A (Molecular Sieve is a trademark) as a synthetic zeolite, thereby obtaining 254.38 g of 2-chloro-1,3,3,3-tetrafluoropropene (1224). As it was purified by distillation with a distillation column filled with Helipack No. 1 and having theoretical 80 stages, there was obtained 192.36 g of a fraction containing 99.81% of cis form (1224Z) and 0.18% of trans form (1224E).

Example 3

Dehydrochlorination Reaction of Fraction B Containing Mainly 234da Erythro Form

Using sodium hydroxide having an acid dissociation constant (pKa) of not less than 15 as an inorganic base and using tetrabutylammonium bromide as a phase transfer catalyst, there was conducted a dehydrochlorination reaction of fraction B containing mainly erythro form of 234da by simple distillation, thereby obtaining 1224 containing mainly cis form (1224Z).

There was prepared a 1 liter capacity, four-necked flask equipped with a Vigreux column having a length of 30 cm, a thermometer, and a stirrer. There was prepared a simple distillation apparatus in which a connecting tube and a 500 ml capacity, three-necked flask equipped with a Dimroth and a dry ice/acetone bath were attached to the top portion of the Vigreux column. The 1 liter capacity, four-necked flask was charged with the fraction (B) (555.27 g, 3.00 mol), prepared in Preparation Example 2 and containing mainly erythro form, and tetrabutylammonium bromide (2.43 g, 0.008 mol) as a phase transfer catalyst. While refluxing the content by allowing a coolant of −15° C. to flow through the Dimroth, a bottom portion of the flask was immersed in a water bath having a water temperature of 35° C., and the content in the flask was stirred. From the dropping funnel, 533.23 g (3.33 mol) of sodium hydroxide aqueous solution having a concentration of 25 mass % was gradually added dropwise to the flask by spending 258 minutes. After terminating the dropping, the water bath temperature was changed to 50° C., and the reaction was continued for 1 hour. After that, a reaction product was recovered in the 500 ml capacity, three-necked flask, thereby obtaining 417.98 g of 2-chloro-1,3,3,3-tetrafluoropropene (1224). Composition of the reaction product was measured by gas chromatography. With this, it was found to be 89.6% of cis form (1224Z) and 10.4% of trans form (1224E).

Example 4

Using sodium hydroxide having an acid dissociation constant (pKa) of not less than 15 as an inorganic base and using tetrabutylammonium bromide as a phase transfer catalyst, there was conducted a dehydrochlorination reaction of 234da erythro form to obtain cis form (1224Z).

A 200 ml capacity, three-necked flask equipped with a Dimroth, a thermometer, and a stirrer was charged with 10.18 g (55 mmol) of 234da (purity of erythro form: 99.7%) and 0.18 g (0.6 mmol) of tetrabutylammonium bromide as a phase transfer catalyst. A bottom portion of the flask was immersed in an iced water bath. While refluxing the content by allowing a coolant of −15° C. to flow through the Dimroth and stirring the inside of the flask, 10.61 g (66 mmol) of sodium hydroxide aqueous solution having a concentration of 25 mass % was gradually added dropwise to the flask from the dropping funnel by spending 33 minutes. Then, after stirring the content in the flask for 2 hours, it was transferred into a separating funnel previously cooled in a refrigerator to achieve a two-layer separation. With this, an organic layer of 5.64 g was obtained. Composition of the organic layer was measured by gas chromatography. With this, it was found to be 99.7% of cis form (1224Z), 0.3% of trans form (1224E), and 0.02% of 1,2-dichloro-3,3,3-trifluoropropene $CF_3CCl=CHCl$ (1223).

Example 5

Using potassium hydroxide having an acid dissociation constant (pKa) of not less than 15 as an inorganic base and using tetrabutylammonium bromide as a phase transfer catalyst, there was conducted a dehydrochlorination reaction of 234da erythro form to obtain cis form (1224Z).

1224 was produced by the same procedure as that of Example 4 by using 14.88 g (66 mmol) of potassium hydroxide aqueous solution having a concentration of 25 mass %, in place of the sodium hydroxide aqueous solution. As a result, it was found to be 99.7% of cis form (1224Z), 0.2% of trans form (1224E), and 0.02% of 1223.

Thus, the results of Examples 1-5 are shown in Table 3.

TABLE 3

| | Raw material compounds (%) | Base | Phase transfer catalyst | Products (%) | | | |
|---|---|---|---|---|---|---|---|
| | | | | trans form 1224E | cis form 1224Z | 1223 | 234da |
| Ex. 1 | Fraction A threo:erythro = 94.2:5.8 | sodium hydroxide not less than 15 of pKa | tetrabutylammonium bromide | 95.5 | 4.5 | Below detection | 0.02 |
| Ex. 2 | Fraction B threo:erythro = 10.1:89.9 | sodium hydroxide not less than 15 of pKa | tetrabutylammonium bromide | 11.1 | 89.0 | Below detection | Below detection |
| Ex. 3 | Fraction B threo:erythro = 10.1:89.9 | sodium hydroxide not less than 15 of pKa | tetrabutylammonium bromide | 10.4 | 89.6 | Below detection | Below detection |

TABLE 3-continued

| | Raw material compounds (%) | Base | Phase transfer catalyst | Products (%) | | | |
|---|---|---|---|---|---|---|---|
| | | | | trans form 1224E | cis form 1224Z | 1223 | 234da |
| Ex. 4 | threo:erythro = 0.3:99.7 | sodium hydroxide not less than 15 of pKa | tetrabutylammonium bromide | 0.3 | 99.7 | 0.02 | Below detection |
| Ex. 5 | threo:erythro = 0.3:99.7 | potassium hydroxide not less than 15 of pKa | tetrabutylammonium bromide | 0.2 | 99.7 | 0.02 | Below detection |

Reference Example 1

Using a tripotassium phosphate aqueous solution ($K_3PO_4$) having an acid dissociation constant (pKa) of 12.3 as an inorganic base and using tetrabutylammonium bromide as a phase transfer catalyst, there was conducted a dehydrochlorination reaction of 234da to obtain 1224.

A 200 ml capacity, three-necked flask equipped with a Dimroth, a thermometer, a dropping funnel and a stirrer was charged with 25.29 g (137 mmol) of 234da, which had been obtained in Preparation Example 1 and had not been subjected to a distillation separation into erythro form and threo form, and 0.42 g (1.3 mmol) of tetrabutylammonium bromide as a phase transfer catalyst. While allowing a coolant of −15° C. to flow through the Dimroth, refluxing the content, and stirring under room temperature (25° C.), 127.48 g (150 mmol) of a tripotassium phosphate aqueous solution having a concentration of 25 mass % was gradually added dropwise to the flask from the dropping funnel by spending 102 minutes. Then, after stirring the content in the flask for 3 hours at room temperature (25° C.), it was transferred into a separating funnel previously cooled in a refrigerator to achieve a two-layer separation. With this, an organic layer of 21.26 g was obtained. Composition of the organic layer was measured by gas chromatography. With this, it was found to be 37.5% of cis form (1224Z), 53.3% of trans form (1224E), 3.0% of 1223, 5.0% of 234da, and 1.2% of unidentified substances (unknown).

Reference Example 2

Using 1,8-diazabicyclo-[5,4,0]-7-undecene (DBU) having an acid dissociation constant (pKa) of 12 as an organic base and using tetrabutylammonium bromide as a phase transfer catalyst, there was conducted a dehydrochlorination reaction of 234da to obtain 1224.

A 200 ml capacity, three-necked flask equipped with a Dimroth, a thermometer, a dropping funnel and a stirrer was charged with 25.03 g (135 mmol) of 234da, which had been obtained in Preparation Example 1 and had not been subjected to a distillation separation into erythro form and threo form. While allowing a coolant of −15° C. to flow through the Dimroth and refluxing the content, a bottom portion of the flask was immersed in an iced water bath. While stirring the content in the flask, 17.6 g (116 mmol) of 1,8-diazabicyclo-[5,4,0]-7-undecene (DBU) was gradually added to the flask from the dropping funnel by spending 50 minutes, thereby obtaining a solid matter. Then, 30.34 g of water was gradually added to the flask by spending 11 minutes to dissolve the solid matter. Then, 12.26 g (118 mol) of hydrochloric acid having a concentration of 35 mass % was gradually added by spending 5 minutes. Then, the content in the flask was transferred into a separating funnel previously cooled in a refrigerator to achieve a two-layer separation, thereby obtaining an organic layer of 18.29 g. Composition of the organic layer was measured by gas chromatography. With this, it was found to be 39.2% of trans form (1224E), 32.5% of cis form (1224Z), 0.2% of 1223, 27.0% of 234da, and 1.1% of unidentified substances (unknown).

Even if not using a phase transfer catalyst, by-production of 1223 was suppressed to 0.2% by using DBU as an organic base.

Reference Example 3

Using potassium hydroxide (KOH) having an acid dissociation constant (pKa) of not less than 15 as an inorganic base, there was conducted a dehydrochlorination reaction of 234da with no use of a phase transfer catalyst, to obtain 1224.

Similar to Example 5, using potassium hydroxide (KOH) having an acid dissociation constant (pKa) of not less than 15 as a base, there was conducted a dehydrochlorination reaction of 234da with no use of a phase transfer catalyst.

A vacuum pump was connected to a 50 ml capacity, glass autoclave equipped with a pressure gauge and a valve, followed by decompression and then closing the valve. A bottom portion of the autoclave was immersed in an iced water bath for cooling. A tube made of tetrafluoroethylene-perfluoroalkylvinyl ether copolymer (in the following, it may be referred to as PFA) was connected to the valve of the autoclave, followed by opening the valve. Then, 10.59 g (57 mmol) of 234da obtained by Preparation Example 1 and not subjected to a distillation separation into erythro form and threo form and then 38.33 g (171 mmol) of a potassium hydroxide aqueous solution having a concentration of 25 mass % were injected into the autoclave. Then, the valve was closed, and continuously under an iced cooling the reaction was conducted while stirring the content for 3 hours. During the reaction the pressure gauge indicated 0.03 MPaG. It was transferred into an analytical funnel previously cooled in a refrigerator to achieve a two-layer separation, thereby obtaining 7.69 g of an organic layer. Composition of the organic layer was measured by gas chromatography. With this, it was found to be 31.1% of trans form (1224E), 37.8% of cis form (1224Z), 29.7% of 1223, 0.2% of 234da, and 1.2% of unidentified substances (unknown).

Even if using potassium hydroxide having an acid dissociation constant (pKa) as an inorganic base, 1223 was produced by 29.69% as a by-product, and, in the case of no use of tetrabutylammonium bromide as a phase transfer catalyst, yield of 1224 as the target product was low.

Reference Example 4

Using potassium hydroxide (KOH) having an acid dissociation constant (pKa) of not less than 15 as an inorganic base, there was conducted a dehydrochlorination reaction of 234da with no use of a phase transfer catalyst, to obtain 1224.

A vacuum pump was connected to a 50 ml capacity, glass autoclave equipped with a pressure gauge and a valve, followed by decompression and then closing the valve. A bottom portion of the autoclave was immersed in an iced water bath for cooling. A tube made of PFA was connected to the autoclave, followed by opening the valve. Then, 10.48 g (57 mmol) of 234da obtained by Preparation Example 1 and not subjected to a distillation separation into erythro form and threo form and then 13.69 g (62 mmol) of a potassium hydroxide aqueous solution having a concentration of 25 mass % were injected into the autoclave. Then, the valve was closed, and continuously under an iced cooling the content was stirred for 3 hours. Upon this, the pressure gauge indicated 0.02 MPaG. It was transferred into an analytical funnel previously cooled in a refrigerator to achieve a two-layer separation, thereby obtaining 6.98 g of an organic layer. Composition of the organic layer was measured by gas chromatography. With this, it was found to be 33.9% of trans form (1224E), 38.3% of cis form (1224Z), 26.7% of 1223, 0.2% of 234da, and 0.9% of unidentified substances (unknown).

Even if using potassium hydroxide having an acid dissociation constant (pKa) of not less than 15 as an inorganic base, 1223 was produced by 26.7% as a by-product, and, in the case of no use of tetrabutylammonium bromide as a phase transfer catalyst, yield of 1224 as the target product was low.

Reference Example 5

Using potassium hydroxide (KOH) having an acid dissociation constant (pKa) of not less than 15 as an inorganic base, there was conducted a dehydrochlorination reaction of 234da with no use of a phase transfer catalyst, to obtain 1224.

A vacuum pump was connected to a 50 ml capacity, glass autoclave equipped with a pressure gauge and a valve, followed by decompression and then closing the valve. A bottom portion of the autoclave was immersed in an iced water bath for cooling. A tube made of PFA was connected to the autoclave, followed by opening the valve. Then, 10.21 g (55 mmol) of 234da obtained by Preparation Example 1 and not subjected to a distillation separation into erythro form and threo form and then 35.81 g (160 mmol) of a potassium hydroxide aqueous solution having a concentration of 25 mass % were injected into the autoclave. Then, the valve was closed, followed by stirring for 30 minutes under room temperature (25° C.). Then, a bottom portion of the autoclave was immersed in an oil bath adjusted to 50° C., and the reaction was conducted with stirring for 3 hours. During the reaction, the pressure gauge indicated 0.12 MPaG. The bottom portion of the autoclave was immersed in an iced water bath for cooling. Then, the reaction product in the autoclave was transferred into an analytical funnel previously cooled in a refrigerator to achieve a two-layer separation, thereby obtaining an organic layer of 7.21 g. Composition of the organic layer was measured by gas chromatography. With this, it was found to be 24.3% of trans form (1224E), 38.3% of cis form (1224Z), 36.2% of 1223, 0.06% of 234da, and 1.2% of unidentified substances (unknown).

Even if using potassium hydroxide having an acid dissociation constant (pKa) of not less than 15 as an inorganic base, with no use of phase transfer catalyst, we have found that 1223 is produced by 36.2% as a by-product, unidentified substances (unknown) are 1.2%, and selectivity of 1224 as the target product is low.

Thus, the results of Reference Examples 1-5 are shown in Table 4.

TABLE 4

| | Raw material compounds (%) | Base | Phase transfer catalyst | Products (%) | | | | |
|---|---|---|---|---|---|---|---|---|
| | | | | trans form 1224E | cis form 1224Z | 1223 | 234da | unknown |
| Ref. Ex. 1 | threo form:erythro form = 65.1:33.7 | tripotassium phosphate pKa: 12.3 | tetrabutylammonium bromide | 53.3 | 37.5 | 3.0 | 5.0 | 1.2 |
| Ref. Ex. 2 | threo form:erythro form = 65.1:33.7 | DBU pKa: 12 | tetrabutylammonium bromide | 39.2 | 32.5 | 0.2 | 27.0 | 1.1 |
| Ref. Ex. 3 | threo form:erythro form = 65.1:33.7 | potassium hydroxide not less than 15 of pKa | none | 31.1 | 37.8 | 29.7 | 0.2 | 1.2 |
| Ref. Ex. 4 | threo form:erythro form = 65.1:33.7 | potassium hydroxide not less than 15 of pKa | none | 33.9 | 38.3 | 26.7 | 0.2 | 0.9 |
| Ref. Ex. 5 | threo form:erythro form = 65.1:33.7 | potassium hydroxide not less than 15 of pKa | none | 24.3 | 38.3 | 86.2 | 0.06 | 1.2 |

In 234da as the raw material compound, the ratio of threo form to erythro form, threo form:erythro form, is 65.1:33.7. In comparison between threo form and erythro form, erythro form is more unstable than threo form due to the difference of steric structure. Therefore, in theory, erythro form is more reactive than threo is. In case that the reaction has not progressed, or in case that yield of 1224 is low by by-production of 1223, erythro form, which is more unstable than threo is, is more reactive with the base. Therefore, it is considered that the proportion of cis form (1224Z) has become large. Furthermore, it is considered that yield of trans form has decreased, because, with no use of phase transfer catalyst, trans form has decomposed by the base to generate unidentified substances (unknown), and then those have moved into the aqueous phase on the two-layer separation.

The invention claimed is:

1. A process for producing 2-chloro-1,3,3,3-tetrafluoropropene (1224), comprising:
   a first step (separation step) that is a separation step for separating 2,3-dichloro-1,1,1,3-tetrafluoropropane (234da) and is a step (1a) for taking out a component (A) having a molar ratio of threo form to erythro form of 100:0 to 80:20 or a step (1b) for taking out a component (B) having a molar ratio of threo form to erythro form of 0:100 to 20:80; and
   a second step of bringing the component (A) or the component (B) into contact with a base.

2. The production process of claim 1, wherein the first step is a step (1a) of taking out a fraction (A) having a molar ratio of threo form to erythro form of 100:0 to 80:20 or a step (1b) of taking out a fraction (B) having a molar ratio of threo form to erythro form of 0:100 to 20:80.

3. The production process of claim 1, wherein the second step is a second step A of bringing component (A) having a molar ratio of threo form to erythro form of 100:0 to 80:20 into contact with the base, thereby obtaining 2-chloro-1,3,3,3-tetrafluoropropene (1224) having a molar ratio of trans form to cis form of 100:0 to 80:20.

4. The production process of claim 1, wherein the second step is a second step B of bringing component (B) having a molar ratio of threo form to erythro form of 0:100 to 20:80 into contact with the base, thereby obtaining 2-chloro-1,3,3,3-tetrafluoropropene (1224) having a molar ratio of trans form to cis form of 0:100 to 20:80.

5. The production process of claim 1, wherein the base has an acid dissociation constant (pKa) of 4.8 or greater.

6. The production process of claim 1, wherein the second step is a step conducted in the presence of a phase transfer catalyst.

7. The production process of claim 1, wherein the base is an organic base.

8. The production process of claim 7, wherein the base is an amine.

9. The production process of claim 1, wherein a reactive distillation is conducted in the second step.

10. A process for separating 2,3-dichloro-1,1,1,3-tetrafluoropropane (234da), in which a distillation of 2,3-dichloro-1,1,1,3-tetrafluoropropane (234da) is conducted, thereby achieving a separation into a fraction (A) having a molar ratio of threo form to erythro form of 100:0 to 80:20 and a fraction (B) having a molar ratio of threo form to erythro form of 0:100 to 20:80.

11. A process for producing a trans form (1224E) of 2-chloro-1,3,3,3-tetrafluoropropene, in which a threo form of 2,3-dichloro-1,1,1,3-tetrafluoropropane (234da) is brought into contact with a base.

12. A process for producing a cis form (1224Z) of 2-chloro-1,3,3,3-tetrafluoropropene, in which an erythro form of 2,3-dichloro-1,1,1,3-tetrafluoropropane (234da) is brought into contact with a base.

* * * * *